United States Patent [19]

Shah et al.

[11] Patent Number: 4,980,155

[45] Date of Patent: Dec. 25, 1990

[54] TWO PHASE COSMETIC COMPOSITION

[75] Inventors: Arvind N. Shah, Howell, N.J.; Ivonne Brown, Roosevelt, N.Y.

[73] Assignee: Revlon, Inc., New York, N.Y.

[21] Appl. No.: 405,513

[22] Filed: Sep. 11, 1989

[51] Int. Cl.$^5$ .............................................. A61K 7/021
[52] U.S. Cl. ...................................... 424/63; 424/70; 424/78; 252/315.01; 514/844; 514/944
[58] Field of Search ............................ 424/63, 78, 70; 252/315.01, 351; 514/844–848, 944

[56] References Cited

U.S. PATENT DOCUMENTS 4,335,103  6/1982  Barker et al. ........................ 424/63

FOREIGN PATENT DOCUMENTS 2352266  4/1975  Fed. Rep. of Germany .
2456048  5/1976  Fed. Rep. of Germany .

*Primary Examiner*—Merrell C. Cashion, Jr.
*Assistant Examiner*—Amy Hulina

[57] ABSTRACT

A two phase cosmetic composition is disclosed. The composition comprises a color phase composition including a film forming agent, at least one colorant, an emulsifier and water. The cosmetic composition also includes a gel phase composition which comprises a water soluble polymer and water. The color phase composition and the gel phase composition, although miscible with each other, are disposed in discrete side by side separate phases. This composition is particularly useful in cosmetic preparations which emphasize color.

42 Claims, No Drawings

TWO PHASE COSMETIC COMPOSITION

BACKGROUND OF THE DISCLOSURE

1. Field of the Invention

Many cosmetic products rely on color to provide beauty enhancement. Thus, such beauty aids as foundation, blush, mascara, brow products and the like rely on color enhancement provided by these products for effectiveness. In view of the criticality of color in such applications it is desirable to present the cosmetic product, which is ultimately applied to the face or other parts of the body to highlight that color, in a way that emphasizes its color. In the past such cosmetic products, if visible at all, were presented as a colored composition. Those skilled in the cosmetic arts appreciate that if the color of the cosmetic composition could be presented in a more dramatic manner, the product would be more desirable to the purchaser. For example, presenting the color in the form of a spiral, swirl or the like, against a background of a clear or color contrasted liquid dramatically emphasizes the attractiveness of the color of the cosmetic beauty aid.

It would be relatively simple to produce an oil based pigment phase in a clear aqueous phase or vice versa. The immiscibility of the two phases would permit the production of a cosmetic product in which the above desired, highly attractive packaging could be provided. However, the inclusion of an oil-based phase would be undesirable for at least two reasons. First, it would be difficult to combine the immiscible phases to form the complete cosmetic composition. Second, even if the two immiscible phases could somehow be combined, the product, containing a non-water soluble phase, might be difficult to remove.

Ideally, a two phase composition should include a color phase and clear or color contrasted gel phase which are miscible. However, when attempts were made to produce such a product in the past a two-phase composition was obtained in which the color phase bled into the gel phase producing a product that was aesthetically unattractive.

Thus, cosmetic products have not been produced in which a color phase, highlighting the tint or color of the cosmetic composition, is disposed as a discrete color phase against a background of a clear or color contrasted gel.

2. Background of the Prior Art

Two phase cosmetic compositions are known in the prior art. U.S. Pat. No. 4,335,103 to Barker et al. discloses a two phase cosmetic cleansing cream composition which includes two separate and stable cosmetic composition phases which, when intimately mixed, yield a cleansing composition that is applicable to the face and other parts of the body. This composition comprises a first cleansing cream phase composition which includes an oil, a thickening agent, an emulsifier and water. The second phase, a gel phase, comprises water or a water soluble material and a thickening agent. The two phase cosmetic cleansing cream compositions are combined in a swirl-like or marble-like pattern within a container such that the cream hard gel phases are generally stable, separate and visibly distinct.

Although the teaching of the '103 patent represents an advance in the art, it does not emphasize a color phase. Colorants easily migrate. As such, the absence of a teaching in the prior art of non-bleeding phases establishes the absence in the art of a two phase cosmetic composition in which the color phase composition highlights the critical color emphasis of the composition.

BRIEF SUMMARY OF THE INVENTION

A new cosmetic composition has now been discovered which permits the packaging of the composition in separate phases, which are disposed in side by side configuration in an attractive pattern such as a spiral, a swirl, a rod, a flower or the like: Such a presentation permits the critical feature of the composition, its color, to be emphasized in a dramatic and pleasing way. At the same time, the water soluble and miscible nature of the two phases that form the cosmetic composition permit the formation of a homogeneous composition, albeit without color bleeding, which upon mixing is applicable to the face and body in the same way as color-providing cosmetic compositions of the prior art that are packaged in a single undramatic single phase.

In accordance with the present invention a two phase cosmetic composition is provided. The composition includes a color phase composition comprising a film forming agent, at least one colorant, an emulsifier and water. The composition also comprises a gel phase composition including a water soluble polymer and water. The color phase composition and the gel phase composition, miscible in each other, are disposed in separate phases.

DETAILED DESCRIPTION

The two phase cosmetic composition of the present invention includes a color phase composition and a gel phase composition which are packaged in side by side separate phases. The two phases of the composition, however, are miscible so that when they are mixed together they form a cosmetic composition which, in prior art embodiments, was packaged in a single phase. The cosmetic composition within the scope of the subject invention is one which imparts color to parts of the body, primarily the face. Cosmetic compositions within the contemplation of the present invention include mascara, foundation, eye shadow, blush, brow product and the like.

The critical color phase composition, which appears in a container as an attractive shape, in side by side configuration with a transparent or contrasted gel phase composition, may be disposed in the form of a spiral, a swirl, a rod, a flower or the like.

The color phase composition includes four essential components the first of which are inorganic colorants and fillers. Colorants within the contemplation of the color phase composition include the inorganic pigments, carmine, bismuth oxychloride, zinc oxide, iron oxides including iron oxide yellow (C.I. 77492), iron oxide red (C.I. 77491) and iron oxide black (C.I. 77499), zinc oxide, ultramarine violet, ultramarine blue, ultraxarine pink, chromium oxide, chromium hydroxide and manganese violet. Preferred fillers include kaolin, mica, talc and silica. These pigments and fillers are defined in detail in the CFTA Cosmetic Ingredient Dictionary, Third Edition, and Third Edition, Supplement, The Cosmetic Toiletry and Fragrance Assn., Inc., Washington, D.C., (1982). In addition to the above pigments and fillers, titanium dioxide may be used as a colorant, a filler or both. It should be appreciated that titanium dioxide as defined by the CFTA Cosmetic Ingredient Dictionary includes both pure $TiO_2$ and iron oxide coated on titanium dioxide coated mica. It is emphasized that the above group of colorants, although preferred, is not exhaustive and other colorants included in the aforementioned CFTA Cosmetic Ingredient Dictionary, Third Edition, are within the contemplation of the present invention.

The colorant component of the color phase composition is provided by at least one of the above colorants. Oftentimes, preferred embodiments of the subject composition include more than one colorant in the color phase composition. Moreover, as stated above, since the above recitation of colorants is not inclusive, other colorants, known in the art, may not only be used alone but also in combination with one or more of the above recited colorants.

Preferably, the colorant of the color phase composition of the cosmetic composition of the present application is present in a concentration of between about 1% and about 60% by weight, based on the total weight of the color phase composition. More preferably, the colorant is present in the color phase composition in a concentration in the range of between about 30% and about 50% by weight, based on the total weight of the color phase composition.

A second essential component of the color phase composition is a film forming agent. The film forming agent, also referred to as a thickening agent, of the color phase composition of the cosmetic composition of this invention is preferably present in a concentration in the range of between about 1% and about 30% by weight, based on the total weight of the color phase composition. More preferably, the film forming agent represents between about 4% and about 10% by weight, based on the total weight of the color phase composition.

Preferred film forming agents for use in the color phase composition include glyceryl rosinate, pentaerythritol rosinate, pentaerythritol tetraabietate, pentaerythritol tetraoctanoate, pentaerythrythritol tetraoleate and pentaerythritol tetrastearate. Of these, glyceryl rosinate, pentaerythrytol rosinate and pentaerythritol tetraabietate are particularly preferred. Of these particularly preferred film forming agents, glyceryl resonate is most preferred.

The third essential component of the color phase composition is an emulsifier. Preferred emulsifiers useful in the color phase composition include a blend of triethanolamine and isostearic acid, a blend of triethanolamine and stearic acid, TEA-stearate, TEA-isostearate and mixtures thereof. These emulsifiers are fully defined in the CTFA Cosmetic Ingredient Dictionary, Third Edition, which is incorporated herein by reference. Of these emulsifiers, a blend of triethanolamine and stearic acid is particularly preferred.

The emulsifier constitutes between about 1% and about 10% by weight, based on the total weight of the color phase composition. The emulsifier, which serves to disperse the colorant and the film forming agent in water, is more preferably present in a concentration of between about 2% and about 5% by weight, based on the total weight of the color phase composition.

The fourth and last essential component of the color phase composition is water. Water is present in the color phase composition in a concentration in the range of between about 10% by weight to about 98% by weight, based on the total weight of the color phase composition. More preferably, the water constituent of the color phase composition is present in a concentration in the range of between about 20% by weight and about 40% by weight, based on the total weight of the color phase composition.

Although the above discussed components are essential, other constituents are preferably included in the color phase composition. Such a preferably included component is a co-emulsifier the co-emulsifier, if present in the composition, is a low hydrophilic lypophilic balance surface active agent such as glycol monostearate, hydroxylated lanolin, polyethylene glycol stearates including PEG-2 stearate, PEG-2 stearate SE, PEG-4 stearate, PEG-5 stearate, PEG-6 stearate, PEG-6-32 stearate, PEG-7 stearate, PEG-8 stearate, PEG-9 stearate, PEG-10 stearate, PEG-12 stearate, PEG-14 stearate, PEG-18 stearate, PEG-20 stearate, PEG-25 stearate, PEG-30 stearate, PEG-32 stearate, PEG-35 stearate, PEG-36 stearate, PEG-40 stearate, PEG-45 stearate, PEG-50 stearate, PEG-75, PEG-90 stearate, PEG-100 stearate, PEG-120 stearate and PEG-150 stearate and polyethylene glycol sorbitan beeswaxes including PEG-6 sorbitan beeswax, PEG-8 sorbitan beeswax and PEG-20 sorbitan beeswax. All of these co-emulsifiers are defined in the CFTA Cosmetic Ingredient Dictionary, Third Ed. which is incorporated herein by reference. Of these preferred emulsifiers, hydroxylated lanolin, PEG-20 sorbitan beeswax and mixtures thereof are particularly preferred.

Co-emulsifiers are present in the color phase composition of the cosmetic composition of this invention in a concentration in the range of between 0.1% and about 5% by weight, based on the total weight of the color phase composition. The co-emulsifier, present in the color phase to stabilize the formulation, and thus insure long shelf life, is more preferably present in the color phase composition in a concentration of between about 0.3% and about 3% by weight, based on the total weight of the color phase composition.

Another component oftentimes present in the color phase composition is a protective colloid. The protective colloid is present to maintain the pigment in suspension. Among the preferred colloids useful in this application are hydroxypropylcellulose, hydroxypropyl methylcellulose, cellulose, cellulose gum, hydroxyethyl cellulose, PVP, PVP/VA copolymer, polyvinyl alcohol, hydroxybutyl methylcellulose, carboxymethyl hydroxyethylcellulose and mixtures thereof. These colloids are fully defined in the CFTA Cosmetic Ingredient Dictionary, Third Edition, which is incorporated herein by reference. Of the colloids preferred for use in the color phase composition, PVP and cellulose gum are particularly preferred.

The protective colloid or colloids component of the color phase composition are usually present in a concentration in the range of between 1% and about 5% by weight, based on the total weight of the color phase composition. More preferably, one or more protective colloids are present in a concentration of between about 1.5% and about 3% by weight, based on the total weight of the color phase composition.

Yet another optional additive included in the color phase composition of the present invention is at least one preservative. The function of preservatives is to prevent decay of the cosmetic composition. Preferred preservatives used in the color phase composition include the parabens, that is, methylparaben, ethylparaben, propylparaben and butylparaben, imidazolidinyl urea, disodium EDTA and trisodium EDTA. These preservatives are defined in detail in the CTFA Cosmetic Ingredient Dictionary, Third Edition, which is incorporated herein by reference. Of these preservatives, methylparaben, propylparaben and mixtures thereof are particularly preferred for use in the color phase composition.

The preservative component is present in the color phase composition in a concentration of between 1% and about 2% by weight, based on the total weight of the color phase composition. More preferably, the preservative component or components is present in the color phase composition in a concentration of between about 0.2% and about 1% by weight, based on the total weight of the color phase composition.

Another optional component of the color phase composition is a humectant. The humectant aids in retarding moisture loss from the color phase composition. The humectant is present in the color phase composition in a concentration in the range of between 10% and about 30% by weight, preferably, between about 20% to about 30% by weight, based on the total weight of the color phase composition. Preferred humectants for use in the color phase compositions include hexylene glycol, propylene glycol and glycerin, humectants defined in the CFTA Cosmetic Ingredient Dictionary, Third Edition which is incorporated herein by reference. Propylene glycol is particularly preferred for use in the color phase composition.

A final optional component of the color phase composition is a neutralizer. A neutralizing agent may be included in the color phase composition to neutralize any acidity imparted thereto by the above discussed components, especially the stearic acid emulsifier and the glyceryl rosinate film forming agent. A particularly preferred neutralizing agent for use in the color phase composition is triethanolamine.

The neutralizer is present in the color phase composition in a concentration in the range of between 0.25% and about 5% by weight, based on the total weight of the color phase composition. Preferably, the neutralizer is present in a concentration in the range of between about 0.75% and about 3% by weight, based on the total weight of the color phase composition.

The second composition of the two phase cosmetic composition of the present invention, is a gel phase composition. The gel phase composition is preferably transparent although it may alternately possess color clearly contrasted from the color of color phase composition. That is, the gel phase composition may be colored. If colored the gel phase is usually white. The gel phase composition whether transparent, white, of another color must be free of the color of the color phase composition. As stated above, there can be no bleeding of the color phase composition into the gel phase composition.

The gel phase composition includes, as an essential component, a water soluble resin. The water soluble resin is preferably a member of the "Carbomer" family of crosslinked acrylic acid polymers The water soluble resin can also be a mixture of polyglycerylmethacrylate and propylene glycol, sold under the tradename, Lubragal, sodium carboxymethyl cellulose, hydroxyethyl cellulose, polyvinyl alcohol, hydroxypropylmethyl cellulose, cellulose gum, PVP and blends thereof. Preferably, the water soluble resin component is Carbomer 910, Carbomer 934, Carbomer 934P, Carbomer 940 or Carbomer 941. These Carbomer polymers are all detailed in the CTFA Cosmetic Ingredient Dictionary, Third Edition which is incorporated herein by reference. It is particularly preferred that the gel phase composition include the water soluble resin, Carbomer 940. Carbomer 940 is a polymer useful in forming a sparkling water clear gel.

The water soluble polymer component comprises between about 0.1% to about 10% by weight based on the total weight of the gel phase composition. More preferably, the water soluble polymeric component comprises between about 0.5% and about 3% by weight, based on the total weight of the gel phase composition.

A second essential component of the gel phase composition is water. Water is present in the gel phase composition in the range of between about 50% by weight and about 98% by weight. More preferably, the water component of the gel phase composition is present in the gel composition in the range of between about 70% by weight and about 95% by weight, based on the total weight of the gel composition.

Other components may optionally also be present in the gel phase composition of the two phase cosmetic composition of this invention. Thus, a preservative is usually included in the gel phase composition, as it is in the color phase composition. Its presence is included in the gel phase composition in a concentration in the range of between about 0.1% by weight and about 1% by weight, based on the total weight of the gel phase composition. More preferably, the preservative is included in a concentration in the range of between about 0.15% and about 0.5% by weight, again based on the total weight of the gel phase composition.

The preservatives useful in the gel phase composition are those cosmetically approved preservatives which are water soluble. Thus, the parabens, especially methylparaben, and imidazolidinyl urea are particularly preferred. Other preservatives that may be used in the gel phase composition include butylparaben, dehydroacetic acid, DMDM hydantoin, ethylparaben, imidazolidinyl urea, propylparaben and sodium benzoate.

Another preferred but optional component of the gel phase composition is a stabilizer which stabilizes the gel phase composition. Preferred stabilizers contemplated for use in the gel phase composition include glycerin and propylene glycol of which glycerin is particularly preferred.

The stabilizer component is preferably present in the gel phase composition in a concentration in the range of between 0.1% by weight and about 3% by weight, based on the total weight of the gel phase composition. More preferably, the stabilizer is present in a concentration in the range of between about 0.2% and about 2% by weight, based on the total weight of the gel phase composition.

A drying agent may also be provided in the gel phase composition. If present in the gel phase composition, the drying agent component represents between 1% and less than about 5% by weight, preferably, between about 3% and about 4.9% by weight, based on the total weight of the gel phase composition.

A preferred drying agent for use in this application is isopropyl alcohol or an SD alcohol. That is, isopropyl alcohol or any of the SD alcohols, SD Alcohol 1 to SD Alcohol 46, listed in the CTFA Cosmetic Ingredient Dictionary, Third Edition, may be used. However, SD Alcohol 40 is particularly preferred for use in the gel phase composition.

Another optional component which may be present in the gel phase composition is a neutralizing agent. The neutralizing agent may be present in a concentration in the range of between about 1% and about 6% by weight, based on the total weight of the gel phase composition. More preferably, the neutralizing agent is present in a concentration in the range of between about 2% and about 4% by weight, based on the total weight of the gel phase composition.

A neutralizing agent is employed in the gel phase composition for the same purpose for which it is used in the color phase composition. It neutralizes the mildly acidic nature of the gel phase composition. In the case of the gel phase composition, this is a more pronounced problem since the major component of this composition is a mildly acidic water soluble polymer. The same preferred neutralizing agent used in the color phase composition, triethanolamine, is preferred for use in the gel phase composition.

Yet another optional component, preferably present in the gel phase composition, is a sequestering agent. A sequestering agent is present in the gel phase composition to insure that impurities, usually in the form of metal ions, present in the water, are removed. This is particularly important in view of the requirement that the gel phase be crystal clear. Preferred sequestering agent for use in the gel phase composition include trisodium EDTA and disodium EDTA. Trisodium EDTA is the sequestering agent of choice for use in the gel phase composition.

The sequestering agent is present in the gel phase composition in a concentration of between about 0.01% and about 0.2% by weight. Preferably, the sequestering agent is present in a concentration in the range of between about 0.01% and about 0.1% by weight, said percentages based on the total weight of the gel phase composition.

Yet another preferred component present in the gel phase composition is a moisturizing agent. The moisturizing agent aids in providing moisture retention. It is present in the gel phase composition in a concentration of between about 0.01% and about 0.2% by weight. Preferably, the moisturizing agent is included in the gel phase composition in an amount representative of between about 0.01% and about 0.1% by weight, said percentages being by weight, based on the total weight of the composition.

Moisturizing agents that can be used in the gel phase composition include hydrolyzed animal protein, hydrolyzed elastin, hydrolyzed keratin, hydrolyzed milk protein, hydrolyzed micropolysaccharides, hydrolyzed silk, potassium coco-hydrolyzed animal protein, and myristoyl hydrolyzed animal protein. Of these, hydrolyzed animal protein is preferred for use in the gel phase composition.

The above recitation of species contemplated for use as the components of the gel phase composition are the CTFA names as set forth in the CTFA Cosmetic Ingredient Dictionary, Third Edition. That dictionary, which provides details of each of the recited species, is incorporated herein by reference.

The two phase compositions, the color phase composition and the gel phase composition, which comprise the subject cosmetic composition, are separately formulated as suggested by the above discussion which separately considers the color phase and gel phase compositions. The two phases are not only separately formulated but are packaged as separate phases in the container in which they are marketed. It is emphasized, however, that the two phases are disposed in discrete side by side phases in the container.

It is this feature which represents a major advance of the cosmetic composition of this invention. The color phase composition, by suitable manipulation, using methods known in the art, may be disposed in a receptacle, that is, a container, a jar, a bottle or the like, in interesting shapes that emphasizes the color of the cosmetic composition against a background of the gel phase composition. The color phase composition may appear as a spiral, a swirl, a rod, a flower or any other desired shape completely engulfed in the gel phase composition. Upon use, however, the two miscible compositions are mixed by the user to form a homogeneous composition which is applied to the face and/or body for its intended cosmetic purpose.

The overall cosmetic composition, including the two separate phase compositions, comprises between about 10% and about 30% by weight of the color phase composition, based on the total weight of the two phase cosmetic composition. Preferably, the color phase composition constitutes between about 15% by weight and about 25% by weight of the two phase cosmetic composition. The gel phase composition comprises between about 70% and about 90% by weight of the total weight of the two phase cosmetic composition. Preferably, the gel phase composition constituency, as a percentage of the two phase cosmetic composition, is between about 75 weight % and about 85 weight %.

Particularly preferred cosmetic compositions are formulated from a gel phase composition which comprises Carboner 940, present in a concentration of between about 53% and about 57%; water, present in a concentration of between about 34% and about 37%; triethanolamine, present in a concentration of between 3% and about 4%; SD Alcohol 40, present in a concentration of between about 4% and about 5%; glycerin, present in a concentration of between about 0.25% and about 1%; methylparaben, present in a concentration of between about 0.1% and about 0.5%; hydrolyzed animal protein, present in a concentration of between about 0.01% and about 0.1%; imidazolidinyl urea, present in a concentration in the range of between about 0.01% and about 0.1%; polyvinyl alcohol, present in a concentration in the range of between about 0.5% and about 1.5%; trisodium EDTA, present in a concentration in the range of between abut 0.01% and about 0.1%; and glycerin, present in a concentration in the range of between about 0.25% and about 1%, all said percentages by weight, based on the total weight of the gel phase composition.

A preferred cosmetic composition is prepared by blending the above gel phase composition with color phase compositions comprising the components present in the concentration ranges recited in the following paragraphs. It is emphasized that the concentration ranges represents percentages by weight, based on the total weight of the color phase composition. It is furthermore emphasized that the following color phase composition is blended with the aforementioned gel phase composition in a weight ratio of between about 15% to about 25% color phase composition and about 75% to about 85% gel phase composition in the two phase cosmetic composition, with a preferred weight ratio of about 20:80, color phase composition to gel phase composition.

The color phase composition is as follows: 50% solution of glyceryl rosinate in isostearyl alcohol, about 2.5% to about 5.5%; propylene glycol, about 23% to about 27%; ultramarine blue, about 15% to about 18%;

iron oxide yellow, about 11% to about 14%; titanium dioxide, about 3.5% to about 6.5%; stearic acid, about 2% to about 4%; PEG-20 sorbitan beeswax, about 1% to about 3%; PVP, about 1% to about 2%; triethanolamine, about 0.5% to about 1.5%; cellulose gum, about 0.3% to about 1%; hydroxylated lanolin, about 0.2% to about 1%; methylparaben, about 0.1% to about 0.4%; propylparaben, about 0.05% to about 0.3%; and water, about 26% to about 30%.

Another preferred color phase composition combined with the above preferred gel phase composition, in a concentration of between about 15% and about 25% by weight, based on the total weight of the two phase cosmetic composition, has the following composition (with percentages being by weight based on the total weight of the color phase composition): 50% solution of glyceryl rosinate in isostearyl alcohol, about 2.5% to about 5.5%; propylene glycol, about 23% to about 25%; water, about 3.0% to about 34%, ultramarine blue, about 23.5% to about 26.5%; iron oxide yellow, about 3% to about 5%; titanium dioxide, about 0.5% to about 1.5%; stearic acid, about 2% to about 4%; PEG-20 sorbitan beeswax, about 1% to about 3%; cellulose gum, about 0.3% to about 1%; triethanolamine, about 0.5% to about 1.5%; PVP, about 1% to about 3%; hydroxylated lanolin, about 0.2% to about 1%; methylparaben, about 0.1% to about 0.4%; and propylparaben, about 0.05% to about 0.3%.

Yet another color phase composition combined with the above preferred gel phase composition, in a concentration of between about 10% and about 40% by weight, based on the total weight of the two phase cosmetic composition, to form a two phase cosmetic composition has the following constituency, with percentages being by weight, based on the total weight of the composition 50% solution of glyceryl rosinate in isostearyl alcohol, about 2.5% to about 5.5%; propylene glycol, about 23% to about 27%; water, about 26% to about 30%; iron oxide black, about 19% to about 21%; iron oxide red, about 4.5% to about 6.5%; iron oxide yellow, about 3% to about 4%; titanium dioxide, about 4% to about 6%; stearic acid, about 2% to about 4%; PEG-20 sorbitan beeswax, about 1% to about 3%; PVP, about 1% to about 3%; triethanolamine, about 0.5% to about 1.5%; cellulose gum, about 0.3% to about 1%; hydroxylated lanolin, about 0.2% to about 1%; methylparaben, about 0.1% to about 0.4%; and propylparaben, about 0.05% to about 0.3%.

Still another cosmetic composition is formed by the preferred gel phase composition and the following color phase composition, with percentages by weight, present in the cosmetic composition in a concentration in the range of about 0% to about 30% by weight, based on the total weight of the cosmetic composition: 50% solution of glyceryl rosinate in isostearyl alcohol, about 2.5% to about 5.5%; propylene glycol, about 23% to about 27%; water, about 29% to about 33%; ultramarine blue, about 28% to about 30%; titanium dioxide, about 0.5% to about 2%; stearic acid, about 2% to about 4%; PEG-20 sorbitan beeswax, about 1% to about 3%; PVP, about 1% to about 3%; triethanolamine, about 1% to about 3%; cellulose gum, about 0.3% to about 1%; hydroxylated lanolin, about 0.2% to about 1%; methylparaben, about 0.1% to about 0.4%; and propylparaben, about 0.05% to about 0.3%.

Yet still another cosmetic composition is formed by the preferred gel phase composition and the following color phase composition, with percentages by weight, present in the cosmetic composition in a concentration in the range of 10% to about 40% by weight, based on the total weight of the cosmetic composition: 50% solution of glyceryl rosinate in isostearyl alcohol, about 2.5% to about 5.5%; propylene glycol, about 23% to about 27%; iron oxide black, about 28% to about 32%; stearic acid, about 2% to about 4%; PEG-20 sorbitan beeswax, about 1% to about 3%; PVP, about 1% to about 3%; triethanolamine, about 1% to about 3%; cellulose gum, about 0.5 to about 1.25%; hydroxylated lanolin, about 0.2% to about 1%; methylparaben, about 0.1% to about 0.4%; and propylparaben, about 0.05% to about 5.5%.

A final preferred two phase cosmetic composition comprises the preferred gel phase composition and the following color phase composition, present in the cosmetic composition in a concentration in the range of between about 15% and about 25% by weight, based on the total weight of the cosmetic composition:

| Component | % by Weight |
| --- | --- |
| 50% solution of glyceryl rosinate in isostearyl alcohol | about 2.5% to about 5.5% |
| propylene glycol | about 23% to about 27% |
| water | about 20% to about 24% |
| ultramarine violet | about 21% to about 25% |
| ultramarine pink | about 12% to about 16% |
| titanium dioxide | about 0.5% to about 2% |
| stearic acid | about 2% to about 4% |
| PEG-20 sorbitan beeswax | about 1% to about 3% |
| PVP | about 1% to about 3% |
| triethanolamine | about 1.5% to about 4% |
| cellulose gum | about 0.005% to about 0.3% |
| hydroxylated lanolin | about 0.2% to about 1% |
| methylparaben | about 0.1% to about 0.4% |
| propylparaben | about 0.05% to about 0.3% |

The following examples rae given to illustrate the scope of the present invention. Because these examples are given for illustrative purposes only, the invention should not be limited thereto.

EXAMPLE 1

Preparation of a Gel Phase Composition

A gel phase composition was prepared by introducing 9.7 parts (by weight) of cold water into steam jacketed homogenizer to which was added 1 part polyvinyl alcohol under agitation. 11 Parts of hot water was added and the contents homogenized for 60 minutes at a temperature of 55° C. to 60° C. until all the PVA was dissolved. To this solution was added glycerin (0.5 part) and trisodium EDTA (0.05 part) while maintaining the same agitation and temperature for 15 minutes. The contents of the homogenizer was filtered and transferred to a jacketed large kettle provided with an agitator. The homogenizer was rinsed with water (about 1 part) and rinsings added to the large kettle. With the temperature of the kettle maintained at 75° C–80° C., a 2.5% aqueous solution of Carbomer 940 was added under agitation to the kettle. When the contents of the large kettle was lump free, the contents were filtered and transferred to a jacketed second kettle provided with propeller agitation. Again, the large kettle was rinsed with about 1 part water and the rinsing added to the third kettle. The third kettle was thereupon heated to 60° C. to 65° C. with agitation. After 15 minutes, a premixed blend of triethanolamine (3.4 parts) and water (2.2 parts) was added to the third kettle contents. The mixture was agitated at 60° C. to 65° C. until a uniform pH of between 7.5 and 8.2 was obtained. At this time, the temperature of the third kettle was decreased to about 30° C. while agitation was maintained. To the contents, maintained at about 30° C, was added a premixed blend of hydroxylated animal protein (0.05 part) and imidazolidinyl urea (0.01 part) in water (1 part). The content of the third kettle was agitated for 10 minutes at about 30° C. when a maitre of 0.2 part methylparaben and 4.5 parts SD Alcohol 40 was introduced. Agitation was continued for about 30 minutes and thereupon the product was discharged into a suitable holding vessel.

The result of this procedure was a transparent gel phase composition having the following composition:

| Component | Concentration % by Wt. |
|---|---|
| 2.5% Carbomer 940 solution in water | 55.0 |
| Water | 35.29 |
| SD Alcohol 40 | 4.5 |
| Triethanolamine | 3.4 |
| Polyvinyl Alcohol | 1.0 |
| Glycerin | 0.5 |
| Methylparaben | 0.2 |
| Hydrolyzed Animal Protein | 0.05 |
| Trisodium EDTA | 0.05 |
| Imidazolidinyl Urea | 0.01 |

EXAMPLE 2

Preparation of a Green Colored Color Phase Composition

A green colored color phase composition was prepared by introducing 23.1 parts (by weight) of water into a steam jacketed, agitator equipped first kettle along with 17 parts of propylene glycol. In this agitated mixture was added 1.5 parts of PVP. A premixed blend of 0.2 part methylparaben and 23 parts propylene glycol was added to the contents of the first kettle, which was maintained at a temperature of 70° to 72° C. under agitation. A premixed blend of 2 parts propylene glycol and 0.6 part cellulose gum was added to the first kettle. A premixed blend of 1 part triethanolamine and 1 part water was next added to the agitated kettle. To this mixture was added 12.73 parts iron oxide yellow, 16.37 parts ultramarine blue and 0.9 part titanium dioxide. Upon dispersion of the colorants, 4.0 parts of titanium dioxide was added thereto and the total contents of the first kettle were passed through a colloid mill into a second kettle also steam-jacketed and provided with agitation means. The colloid mill was rinsed with 4 parts water and the rinsings added to the contents of the second kettle, maintained at a temperature of 78° C. to 82° C. with agitation.

A third steam jacketed kettle equipped with an agitator was charged with 3 parts stearic acid, 2 parts PEG-20 sorbitan beeswax, 4 parts of a solution of glyceryl rosinate in isostearyl alcohol, 0.5 part hydroxylated lanolin and 0.1 part propylparaben. The mixture was heated to 80° to 87° C. whereupon the components melted. Once a liquid, agitation was provided. The contents of the third kettle were next transferred into the second kettle, the contents of which were maintained at 80° C. to 85° C. The resultant composition was mixed under agitation.

The mixture in the second kettle was cooled to 70° C. to 72° C. and 3 parts propylene glycol was added to the liquid composition. The composition was cooled to 28° C. to 30° C. and removed from the kettle. The resultant composition had the following composition.

| Component | Concentration, % by Wt. |
|---|---|
| 50% Solution of Glyceryl Rosinate in Isostearyl Alcohol | 4.0 |
| Propylene Glycol | 25.0 |
| Ultramarine Blue | 16.37 |
| Iron Oxide Yellow | 12.73 |
| Titanium Dioxide | 4.9 |
| Stearic Acid | 3.0 |
| PEG-20 Sorbitan Beeswax | 2.0 |
| PVP | 1.5 |
| Triethanolamine | 1.0 |
| Cellulose Gum | 0.6 |
| Hydroxylated Lanolin | 0.5 |
| Methylparaben | 0.2 |
| Propylparaben | 0.1 |
| Water | 28.1 |

EXAMPLE 3

Preparation of a Teal Colored Color Phase Composition

A teal colored color phase composition was prepared in accordance with the procedure of Example 2. The resultant composition included the following components in the following concentrations:

| Component | Concentration, % by Wt. |
|---|---|
| 50% Solution of Glyceryl Rosinate in Isostearyl Alcohol | 4.0 |
| Propylene Glycol | 25.0 |
| Ultramarine Blue | 25.0 |
| Iron Oxide Yellow | 4.0 |
| Titanium Dioxide | 1.0 |
| Stearic Acid | 3.0 |
| PEG-20 Sorbitan Beeswax | 2.0 |
| Cellulose Gum | 0.6 |
| Triethanolamine | 1.0 |
| PVP | 1.5 |
| Hydroxylated Lanolin | 0.5 |
| Methylparaben | 0.2 |
| Propylparaben | 0.1 |
| Water | 32.1 |

EXAMPLE 4

Preparation of a Brown Colored Color Phase Composition

A brown colored color phase composition was prepared in accordance with the procedure of Example 2. The resultant composition included the following components in the following concentrations:

| Composition | Concentration, % by Wt. |
|---|---|
| 50% Solution of Glyceryl Rosinate in Isostearyl Alcohol | 4.0 |
| Propylene Glycol | 25.0 |
| Iron Oxide Black | 19.9 |
| Iron Oxide Red | 5.5 |
| Iron Oxide Yellow | 3.6 |
| Titanium Dioxide | 5.0 |
| Iron Oxide | 4.0 |
| Stearic Acid | 3.0 |
| PEG-20 Sorbitan Beeswax | 2.0 |
| PVP | 1.5 |
| Triethanolamine | 1.0 |
| Cellulose Gum | 0.6 |
| Hydroxylated Lanolin | 0.5 |
| Methylparaben | 0.2 |
| Propylparaben | 0.1 |

-continued

| Composition | Concentration, % by Wt. |
|---|---|
| Water | 28.1 |

EXAMPLE 5

Preparation of a Blue Colored Color Phase Composition

A blue colored color phase composition was prepared in accordance with the procedure of Example 2. The resultant composition included the following components in the following concentrations:

| Component | Concentration, % by Wt. |
|---|---|
| 50% Solution of Glyceryl Rosinate in Isostearyl Alcohol | 4.0 |
| Propylene Glycol | 25.0 |
| Ultramarine Blue | 29.1 |
| Titanium Dioxide | 0.9 |
| Stearic Acid | 3.0 |
| PEG-20 Sorbitan Beeswax | 2.0 |
| PVP | 1.5 |
| Triethanolamine | 1.5 |
| Cellulose Gum | 0.6 |
| Hydroxylated Lanolin | 0.5 |
| Methylparaben | 0.2 |
| Propylparaben | 0.1 |
| Water | 31.6 |

EXAMPLE 6

Preparation of a Black Colored Color Phase Composition

A black colored color phase composition was prepared in accordance with the procedure of Example 2. The resultant composition included the following components in the following concentrations:

| Component | Composition, % by Wt. |
|---|---|
| 50% Solution of Glyceryl Rosinate in Isostearyl Alcohol | 4.0 |
| Propylene Glycol | 25.0 |
| Iron Oxide Black | 30.0 |
| Stearic Acid | 3.0 |
| PEG-20 Sorbitan Beeswax | 2.0 |
| Triethanolamine | 1.0 |
| PVP | 1.5 |
| Cellulose Gum | 0.75 |
| Hydroxylated Lanolin | 0.5 |
| Methylparaben | 0.2 |
| Propylparaben | 0.1 |
| Water | 31.95 |

EXAMPLE 7

Preparation of a Violet Colored Color Phase Composition

A violet colored color phase composition was prepared in accordance with the procedure of Example 2. The resultant composition included the following components in the following concentrations:

| Component | Concentration, % by Wt. |
|---|---|
| 50% Solution of Glyceryl Rosinate in Isostearyl Alcohol | 4.0 |
| Propylene Glycol | 25.0 |
| Ultramarine Violet | 23.14 |
| Ultramarine Pink | 14.16 |

-continued

| Component | Concentration, % by Wt. |
|---|---|
| Titanium Dioxide | 1.2 |
| Stearic Acid | 3.0 |
| PEG-20 Sorbitan Beeswax | 2.0 |
| PVP | 1.5 |
| Triethanolamine | 2.5 |
| Cellulose Gum | 0.125 |
| Hydroxylated Lanolin | 0.5 |
| Methylparaben | 0.2 |
| Propylparaben | 0.1 |
| Water | 22.575 |

EXAMPLE 8

Preparation of a Green Colored Two Phase Mascara Composition

A green colored mascara composition comprising the green colored color phase composition of Example 2 and the gel phase composition of Example 1 was prepared by separately dispensing the two compositions into a bottle such that the green colored color phase composition appeared as a green colored spiral surrounded by the transparent gel phase composition spiral. There was rot visible bleeding of the color of the spiral into the transparent gel.

In this composition the color phase composition of Example 2 comprised about 20% by weight and the gel phase composition of Example 1 comprised about 80% by weight, based on the total weight of the two phase mascara composition.

EXAMPLE 9

Preparation of a Teal Colored Two Phase Mascara Composition

A teal colored mascara composition comprising the teal colored color phase composition of Example 3 and the gel phase composition of Example 1 was prepared in accordance with the procedure of Example 8 wherein a teal colored spiral surrounded by the transparent phase composition, with no visible bleeding of the color cf the spiral into the transparent gel, was produced.

EXAMPLE 10

Preparation of a Brown Colored Two Phase Mascara Composition

A brown colored mascara composition comprising the brown colored color phase composition of Example 4 and the gel phase composition of Example 1 was prepared in accordance with the procedure of Example 8 wherein a brown colored spiral surrounded by the transparent gel phase composition, with no visible bleeding of the color of the spiral into the transparent gel, was produced.

EXAMPLE 11

Preparation of a Blue Colored Two Phase Mascara Composition

A blue colored mascara composition comprising the blue colored color phase composition of Example 5 and the gel phase composition of Example 1 was prepared in accordance with the procedure of Example 8 wherein a blue colored spiral surrounded by the transparent gel phase composition, with no visible bleeding of the color cf the spiral into the transparent gel, was produced.

EXAMPLE 12

Preparation of a Black Colored Two Phase Mascara Composition

A black colored mascara composition comprising the black colored color phase composition of Example 6 and the gel phase composition of Example 1 was prepared in accordance with the procedure of Example 8 wherein a black colored spiral surrounded by the transparent gel phase composition, with no visible bleeding of the color of the spiral into the transparent gel, was produced.

EXAMPLE 13

Preparation of a Violet Colored Two Phase Mascara Composition

A violet colored mascara composition comprising the violet colored color phase composition of Example 7 and the gel phase composition of Example 1 was prepared in accordance with the procedure of Example 8 wherein a violet colored spiral surrounded by the transparent gel phase composition, with no visible bleeding of the color of the spiral into the transparent gel, was produced.

The above preferred embodiments and examples are given to illustrate the scope and spirit of the present invention. These embodiments and examples will make apparent, to those skilled in the art, other preferred embodiments and examples. These other preferred embodiments and examples are within the contemplation of the present invention. Therefore, the present invention should be limited only by the appended claims.

What is claimed is:

1. A two phase cosmetic composition comprising about 10-30% by weight of the total composition of a color phase composition, said color phase composition comprising a film-forming agent selected from the group consisting of glyceryl rosinate, pentaerythritol rosinae, pentaerythritol tetraabietate pentaerythritol tetrastearate, at least one colorant, about 1-10% by weight of the total weight of the color composition of emulsifier selected from the group consisting of TEA-isostearicacid, TEA-stearic acid, TEA-stearate, or TEA-isostearate and about 10-98% by weight of the total weight of the color composition of water, and about 70-90% by weight of the total composition of a gel phase composition, containing about 0.1-10% by weight of the total weight of the gel composition of water soluble polymer and about 50-98% by weight of the total weight of the color composition of water, said color phase composition and said gel phase composition, miscible in each other, disposed in discrete side by side separate phases.

2. A composition in accordance with claim 1 wherein said film-forming agent component of said color phase composition is present in a concentration in the range of between about 1% and about 30%; said colorant component of said colorphase in a consentration in the range of betwen about 1% and about 60%; all said percentages being by weight, based on the total weight of the color phase composition.

3. A composition in accordance with claim 2 wherein said film forming agent is present in a concentration in the range of between about 4% and about 10%; said colorant is present in a concentration in the range of between about 30% and about 50%; said emulsifier is present in a concentration in he range of between about 2% and about 5%; and said water is present in a concentration in the range of between about 20% and about 40%; all said percentages being by weight, based on the total weight of the color phase composition.

4. A composition in accordance with claim 1 wherein said film forming agent is glyceryl rosinate.

5. A composition in accordance with claim 1 wherein said colorant is selected from the group consisting of ultramarine blue, ultramarine violet, ultramarine pink, iron oxide yellow, iron oxide red, iron oxide black, titanium dioxide and mixtures thereof.

6. A composition in accordance with claim 1 wherein said emulsifier is a blend of stearic acid and triethanolamine.

7. A composition in accordance with claim 1 wherein said color phase composition includes a co-emulsifier present in said color phase composition in a concentration in the range of between 0.1% and about 5% by weight, based on the total weight of said color phase composition.

8. A composition in accordance with claim 7 wherein said co-emulsifier is selected from the group consisting of hydroxylated lanolin, PEG-20.sorbitan beeswax and mixtures thereof, present in said color phase composition in a concentration of between about 0.3% and about 3% by weight, based on the total weight of said color phase composition.

9. A composition in accordance with claim 1 wherein said color phase composition includes a protective colloid present in said color phase composition in a concentration in the range of between 1% and about 5% by weight, based on the total weight of said color phase composition.

10. A composition in accordance with claim 9 wherein said protective colloid is selected from the group consisting of PVP, cellulose gum and mixtures thereof, present in said color phase composition in a concentration of between about 1.5% and about 3% by weight, based on the total weight of the color phase composition.

11. A composition in accordance with claim 1 wherein said color phase composition includes at least one preservative present in a concentration in the range of between 0.1% and about 2% by weight, based on the total weight of said color phase composition.

12. A composition in accordance with claim 11 wherein said preservative is selected from the group consisting of methylparaben, propylparaben and mixtures thereof, present in a concentration in the range of between about 0.2% and about 1% by weight, based on the total weight of said color phase composition.

13. A composition in accordance with claim 1 wherein said color phase composition includes a humectant present in a concentration in the range of between 10% and about 30% by weight, based on the total weight of said color phase composition.

14. A composition in accordance with claim 13 wherein said humectant is propylene glycol, present in a concentration in the range of between about 20% and about 30% by weight, based on the total weight of said color phase composition.

15. A composition in accordance with claim 1 wherein said color phase composition includes a neutralizing agent present in a concentration in the range of between 0.25% and about 5% by weight, based on the total weight of said color phase composition.

16. A composition in accordance with claim 15 wherein said neutralizing agent is triethanolamine, present in a concentration in the range of between about 0.75% and about 3% by weight, based on the total weight of said color phase composition.

17. A composition in accordance with claim 1 wherein said water soluble polymer component of said gel phase composition is present in a concentration of between about 30% and about 80%; and said water component of said gel phase composition is present in a concentration of between about 20% and about 50%, said percentages being by weight, based on the total weight of said gel phase composition.

18. A composition in accordance with claim 17 wherein said water soluble polymer is present in a concentration in the range of between about 40% and about 70% by weight and said water is present in a concentration in the range of between about 25% and about 45% by weight, said percentages based on the total weight of said gel phase composition.

19. A composition in accordance with claim 1 wherein said gel phase composition includes a preservative present in a concentration in the range of between 0.1% and about 1% by weight, based on the total weight of said gel phase composition.

20. A composition in accordance with claim 19 wherein said preservative is selected from the group consisting of methylparaben, imidazolidinyl urea and mixtures thereof, present in a concentration in the range of between about 0.1% and abut 0.5% by weight, based on the total weight of said gel phase composition.

21. A composition in accordance with claim 1 wherein said gel phase composition includes a stabilizer present in a concentration in the range of between 0.1% and about 3% by weight, based on the total weight of said gel phase composition.

22. A composition in accordance with claim 21 wherein said stabilizer is glycerin, present in a concentration in the range of between about 0.2% and about 2% by weight, based on the total weight of said gel phase composition.

23. A composition in accordance with claim 1 wherein said gel phase composition includes a drying agent present in a concentration in the range of between about 1% and less than about 5% by weight, based on the total weight of said phase composition.

24. A composition in accordance with claim 23 wherein said drying agent is SD Alcohol 40, present in a concentration in the range of between about 3% and about 4.9% by weight, based on the total weight of said gel phase composition.

25. A composition in accordance with claim 1 wherein said gel phase composition includes a neutralizer present in a concentration of between about 1% and about 6% by weight, based on the total weight of said gel phase composition.

26. A composition in accordance with claim 25 wherein said neutralizer is triethanolamine, present in a concentration in the range of between about 2% and about 4% by weight, based on the total weight of said gel phase composition.

27. A composition in accordance with claim 1 wherein said gel phase composition includes a sequestering agent present in a concentration of between about 0.01% and about 0.2% by weight, based on the total weight of said gel phase composition.

28. A composition in accordance with claim 27 wherein said sequestering agent is trisodium EDTA, present in a concentration in the range of between about 0.01% and about 0.1% by weight, based on the total weight of said gel phase composition.

29. A composition in accordance with claim 1 wherein said gel phase composition includes a moisturizing agent present in a concentration of between about 0.01% and about 0.2% by weight, based on the total weight of the gel phase composition.

30. A composition in accordance with claim 29 wherein said moisturizing agent is hydrolyzed animal protein, present in a concentration of between about 0.01% and about 0.1% by weight, based on the total weight of said gel phase composition.

31. A composition in accordance with claim 1 wherein said color phase composition comprises between about 10% and about 30% and said gel phase composition comprises between about 70% and about 90%, said percentages being by weight, based on the total weight of said two phase cosmetic composition.

32. A composition in accordance with claim 31 wherein said color phase composition comprises between about 15% and about 25% and said gel phase composition comprises between about 75% and about 85%, said percentages being by weight, based on the total weight of the two phase cosmetic composition.

33. A two phase cosmetic composition comprising:
a color phase composition and a gel phase composition, said color phase composition and said gel phase composition both being water based, miscible in each other and disposed in side by side separate phase configuration;
said color phase composition comprising glyceryl rosinate, present in a concentration in the range of between about 1% by weight and about 30% by weight; at least one colorant, present in a concentration in the range of between about 1% by weight and about 60% by weight; stearic acid, present in a concentration in the range of between about 1% and about 10% by weight; and water, present in a concentration of between about 10% by weight and about 98% by weight, said percentages based on the total weight of said color phase composition; said color phase composition present in said cosmetic composition in a concentration in the range of between about 10% by weight and about 30% by weight, based on the total weight of the cosmetic composition; and said gel phase composition comprising Carbomer 940 which is a polymer of acrylic acid cross-linked with a polyfunctional agent, present in a concentration in the range of between about 30% by weight and about 80% by weight; and water, present in a concentration in the range of between about 20% by weight and about 50% by weight, said- percentages based on the total weight of said gel phase composition; said gel phase composition present in said cosmetic composition in a concentration in the range of between about 70% by weight and about 90% by weight, based on the total weight of said cosmetic composition.

34. A concentration in accordance with claim 33 wherein said color phase composition comprises between about 15% and about 25% by weight, based on the total weight of said cosmetic composition, and wherein said glyceryl rosinate is present in a concentration in the range of between about 4% and about 10%; said colorant is present in a concentration in the range of between about 30% and about 50% by weight; said stearic acid is present in a concentration of between about 2% and about 5% by weight; and said water is present in a concentration in the range of between about 20% and about 40% by weight, said percentages based on the total weight of said color phase composition; and said gel phase composition comprises between about 75% and about 85% by weight, based on the total weight of said cosmetic composition, and wherein said Carbomer 940 which is a polymer of acrylic acid crosslinked with a polyfunctional agent, is present in a concentration in the range of between about 40% and about 70% by weight; and said water is present in a concentration in the range of between about 25% and about 45% by weight, said percentages based on the total weight of said gel phase composition.

35. A composition in accordance with claim 34 wherein said gel phase composition comprises Carbomer 940 which is a polymer of acrylic acid crosslinked with a polyfunctional agent, present in a concentration of between about 53% and about 57%; water, present in a concentration of between about 34% to about 37%; triethanolamine, present in a concentration of between about 3% and about 4% ; SD Alcohol 40, present in a concentration of between about 4% and about 5%; glycerin, present in a concentration in the range of between about 0.25% to about 1%, methylparaben, present in a concentration of between about 0.1 to about 0.5%; hydrolyzed animal protein, present in a concentration in the range of between about 0.01% and about 0.1%; imidazolidinyl urea, present in a concentration in the range of between about 0.01% and about 0.1%; polyvinyl alcohol, present in a concentration in the range of between about 0.5% and about 1.5%; trisodium EDTA, present in a concentration in the range of between about 0.01% and about 0.1%; said percentages being by weight, based on the total weight of the gel composition.

36. A composition in accordance with claim 35 wherein said color phase composition comprises a 50% solution of glyceryl rosinate in isostearyl alcohol, present in said color phase composition in a concentration of about 2.5% to 5.5% by weight; and propylene glycol present in a concentration in the range of between about 23% to about 27% by weight.

37. A composition in accordance with claim 36 wherein said color phase composition additionally comprises water, present in a concentration in the range of between about 26% and about 30%; ultramarine blue, present in a concentration in the range of between about 15% and about 18%; iron oxide yellow, present in a concentration in the range of between about 11% and about 14%; titanium dioxide. present in a concentration in the range of between about 3.5% and about 6.5%; cellulose gum, present in a concentration in the range of between about 0.3% and about 1%; triethanolamine, present in a concentration in the range of between about 0.5% and about 1.5%; PVP, present in a concentration in the range of between about 1% and about 2%; stearic acid, present in a concentration in the range of between about 2% and about 4%; PEG-20 sorbitan beeswax present in a concentration in the range of between about 1% and about 3%; hydroxylated lanolin, present in a concentration in the range of between about 0.2% and about 1%; methylparaben, present in a concentration in the range of between about 0.1% and about 0.4%, and propylparaben, present in a concentration in the range of between about 0.05% and about 0.3%, said percentages being by weight, based on the total weight of said gel phase composition; said color phase composition comprising between about 15% by weight and about 25% by weight based on the total weight of the cosmetic composition.

38. A composition in accordance with claim 36 wherein said color phase composition comprises about 30% and about 34% water; 2% and about 4% stearic acid; about 1% to about 3% PVP; about 23.5% to about 26.5% ultramarine blue; about 3% to about 5% iron oxide yellow; about 0.5% to about 1.5% titanium dioxide; about 0.3% to about 1% cellulose gum; about 0.5% to about 1.5% triethanolamine; about 1% to about 3% PEG-20 sorbitan beeswax; about 0.2% to about 1% hydroxylated lanolin; about 0.2 to about 1% methylparaben; and about 0.1% to about 0.4% propylparaben, said color phase composition present in said cosmetic composition in a concentration in the range of between about 15% and about 25%, based on the total weight of the cosmetic composition.

39. A composition in accordance with claim 36 wherein said color phase composition additionally includes between about 26% and about 30% water; about 19% to about 21% iron oxide black; about 4.5% to about 6.5% iron oxide red; between about 3% and about 4% iron oxide yellow; between about 4% and about 6% titanium dioxide; between about 2% and about 4% stearic acid; between about 1% and about 3% PEG-20 sorbitan beeswax; between about 1% and about 3% PVP; about 0.5% and about 1.5% triethanol-amine; between about 0.3% and about 1% cellulose gum; between about 0.2% and about 1% hydroxylated lanolin; between about 0.1% and about 0.4% methylparaben; and between about 0.05% and about 0.3% propylparaben, said color phase composition comprising between about 15% and about 25% by weight, based on the total weight of the cosmetic composition.

40. A composition in accordance with claim 36 wherein said color phase composition additionally includes between about 29% and about 33% water; about 28% to about 30% ultramarine blue; about 0.5% to about 2% titanium dioxide; about 2% to about 4% stearic acid; about 1% to about 3% PEG-20 sorbitan beeswax; about 1% to about 3% PVP; about 1% to about 3% triethanoloamine; about 0.3% to about 1% cellulose gum; about 0.2% to about 1% hydroxylated lanolin; about 0.1% to about 0.4% methylparaben; and about 0.05% to about 0.3% propylparaben, said color phase composition comprising between about 15% and about 25% by weight, based on the total weight of the cosmetic composition.

41. A composition in accordance with claim 36 wherein said color phase composition additionally includes between about 30% and about 34% water; about 28% to about 32% iron oxide black; about 2% to about 4% stearic acid; about 1% to about 3% PEG-20 sorbitan beeswax; about 1% to about 3% PVP; about 1% to about 3% triethanoloamine; about 0.5% to about 1.25% cellulose gum; about 0.2% to about 1% hydroxylated lanolin; about 0.1% to about 0.4% methylparaben; and about 0.05% to about 0.3% propylparaben; said color phase composition comprising between about 15% and about 25% by weight, based on the total weight of the cosmetic composition.

42. A composition in accordance with claim 36 wherein said color phase composition additionally includes between about 20% and about 24% water; about 21% to about 25% ultramarine violet; about 12% to about 16% ultramarine pink; about 0.5% to about 2% titaniux dioxide; about 2% to about 4% stearic acid; about 1% to about 3% PEG-20 sorbitan beeswax; about 1% to about 3% PVP; about. 1.5% to about 4% triethanoloamine; about 0.05% to about 0.3% cellulose gum; about 0.2% to about 1% hydroxylated lanolin; about 0.1% to about 0.4% methylparaben; and about 0.05% to about 0.3% propylparaben, said color phase composition comprising between about 15% and about 25% by weight, based on the total weight of the cosmetic composition.

* * * * *